(12) United States Patent
St Amant, III et al.

(10) Patent No.: US 9,410,871 B1
(45) Date of Patent: Aug. 9, 2016

(54) APPARATUS FOR ANALYTICAL SAMPLING AND/OR CONDITIONING OF A PROCESS GAS WITH SELECTIVE ISOLATION CAPABILITY, AND METHOD THEREFORE

(71) Applicant: A+ Manufacturing, LLC, Gonzales, LA (US)

(72) Inventors: Valmond Joseph St Amant, III, St Amant, LA (US); Steven Douglas Calverley, Denham Springs, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 344 days.

(21) Appl. No.: 14/060,382

(22) Filed: Oct. 22, 2013

Related U.S. Application Data

(60) Provisional application No. 61/716,656, filed on Oct. 22, 2012.

(51) Int. Cl.
  *G01N 1/22* (2006.01)
  *G01N 1/20* (2006.01)

(52) U.S. Cl.
  CPC ............ *G01N 1/2247* (2013.01); *G01N 1/2035* (2013.01); *G01N 2001/2057* (2013.01); *G01N 2001/2071* (2013.01)

(58) Field of Classification Search
  CPC .............. G01N 1/2035; G01N 2001/2057; G01N 2001/205; G01N 24/085; G01N 1/10; G01N 2001/1025; G01N 2001/105; G01N 2001/2071; G01N 2001/2085
  See application file for complete search history.

(56) References Cited

U.S. PATENT DOCUMENTS

| | | | | |
|---|---|---|---|---|
| 2,736,201 A * | 2/1956 | Ohlsen et al. | ........... | E21B 43/00 166/52 |
| 3,084,554 A * | 4/1963 | Perilloux | ............. | G01N 1/2035 137/599.11 |
| 3,184,973 A * | 5/1965 | Bradley | ............... | G01N 1/2035 73/863.24 |
| 3,282,113 A * | 11/1966 | Sachnik | .................. | F16L 55/00 73/863.02 |
| 3,439,897 A * | 4/1969 | Priese | ..................... | F16K 5/202 251/170 |
| 3,726,143 A * | 4/1973 | Enarsson | ............. | G01N 1/2035 73/863.83 |
| 4,147,062 A * | 4/1979 | Jaeger | .................. | G01N 1/2035 73/863.83 |
| 4,262,533 A * | 4/1981 | Jaeger | .................. | G01N 1/2035 73/863.11 |
| 4,262,534 A * | 4/1981 | Morrison | .................. | B01L 3/02 73/863.86 |
| 4,307,620 A * | 12/1981 | Jiskoot | ................. | G01N 1/2035 73/863.61 |

(Continued)

*Primary Examiner* — David A Rogers
(74) *Attorney, Agent, or Firm* — Joseph T Regard Ltd plc

(57) ABSTRACT

A system for sampling and/or conditioning a process gas such as natural gas or the like with selective isolation capability. The preferred embodiment of the present invention is designed to be OSHA compliant, contemplating a system to insert, retract, maintain and service analytical sample conditioning components or the like in fluid communication with a pressurized pipeline, but upstream an isolation component such as, for example, a double block and bleed sample valve or the like. The preferred embodiment of the present invention thereby provides an apparatus and method for selective isolation of existing or potential hazardous energies which may be associated with the pressurized pipeline and fluids therein from upstream the modular sample component(s) or the like therein.

50 Claims, 9 Drawing Sheets

(56) References Cited

U.S. PATENT DOCUMENTS

| | | | | |
|---|---|---|---|---|
| 4,475,410 A * | 10/1984 | Jaeger | ................ | G01N 1/2035 73/863.84 |
| 4,580,452 A * | 4/1986 | Masson | ................ | F17D 3/10 73/863.86 |
| 4,744,255 A * | 5/1988 | Jaeger | ................ | G01N 1/2035 222/275 |
| 4,887,472 A * | 12/1989 | Jansen | ................ | G01N 1/2035 73/863.86 |
| 4,957,706 A * | 9/1990 | Romette | ................ | G01N 1/10 137/625.12 |
| 5,085,086 A * | 2/1992 | Johnson | ................ | G01N 1/2035 73/863.86 |
| 5,129,267 A * | 7/1992 | Nicholls | ................ | G01N 1/2035 324/321 |
| 5,301,560 A * | 4/1994 | Anderson | ................ | G01N 1/2035 73/863.86 |
| 5,587,539 A * | 12/1996 | Carpenter | ................ | G01N 1/20 73/863.52 |
| 5,629,471 A * | 5/1997 | King | ................ | G01N 1/14 73/1.01 |
| 5,948,998 A * | 9/1999 | Witte | ................ | C12M 33/00 73/863.57 |
| 6,289,752 B1 * | 9/2001 | Nimberger | ................ | G01N 1/2035 73/863.11 |
| 8,701,509 B2 * | 4/2014 | Anders | ................ | G01N 1/18 73/19.06 |
| 8,726,747 B2 * | 5/2014 | Kennett | ................ | G01N 1/2035 73/863.11 |
| 9,151,700 B2 * | 10/2015 | Gransæther | ................ | G01N 1/2035 |
| 9,194,502 B2 * | 11/2015 | Decker | ................ | F16K 3/246 |
| 2007/0272038 A1 * | 11/2007 | Schadt | ................ | G01N 1/2035 73/864.01 |
| 2009/0013805 A1 * | 1/2009 | Zollinger | ................ | G01N 1/2035 73/863.86 |

* cited by examiner

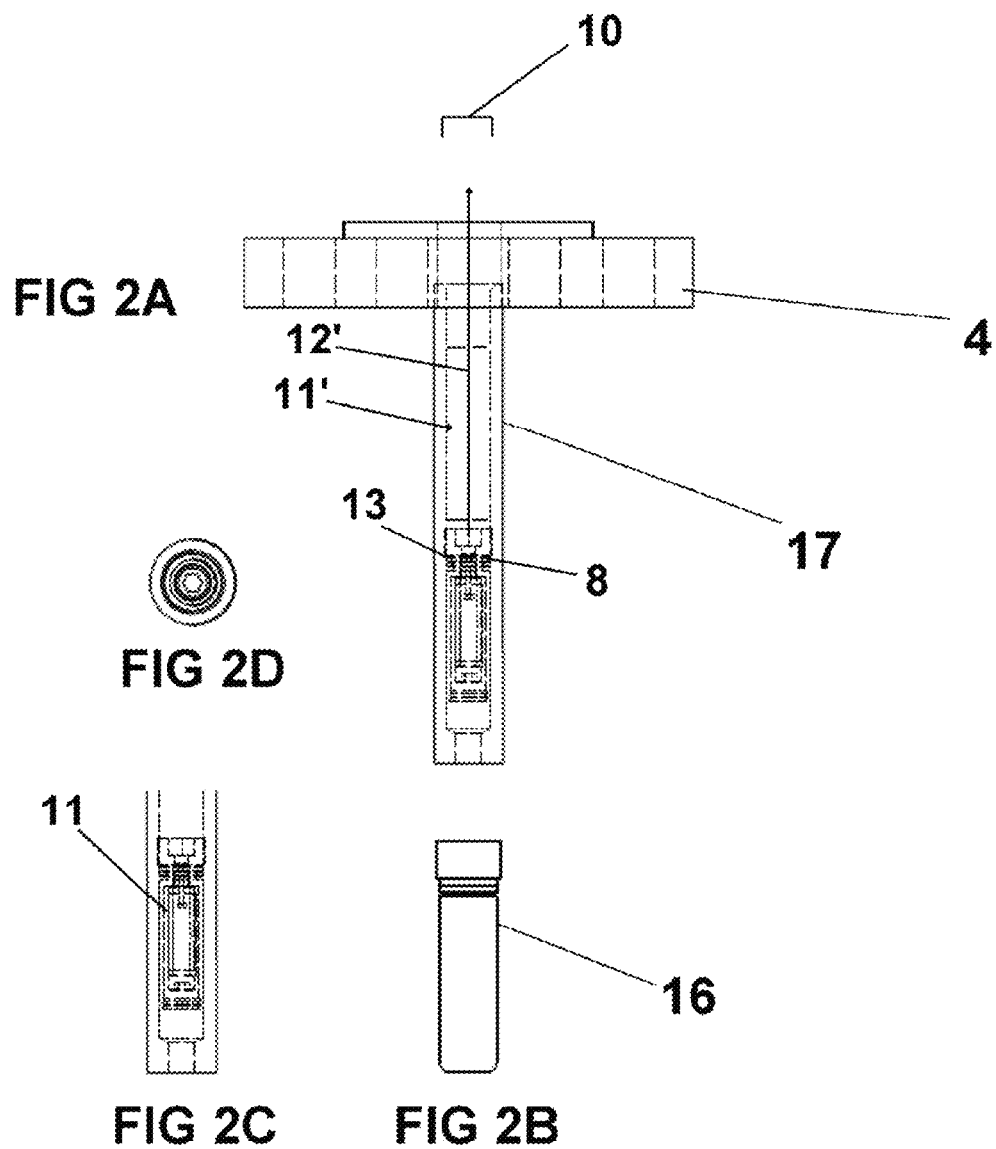

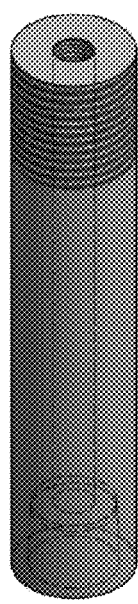
FIG 4A
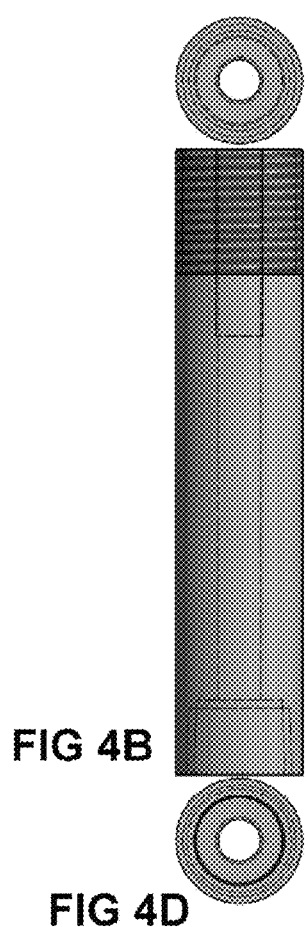
FIG 4C
FIG 4B
FIG 4D
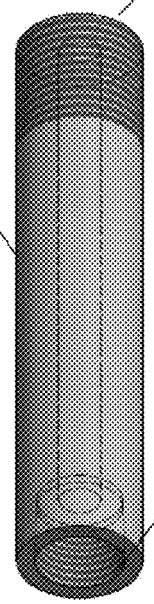
3
2
3'
FIG 4E

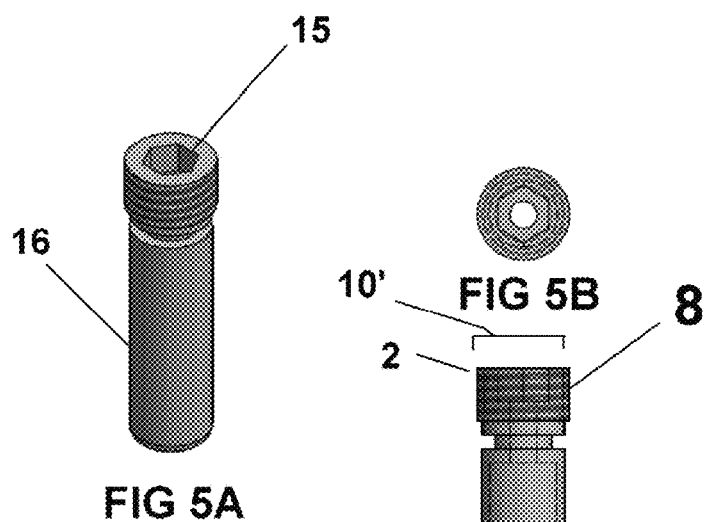
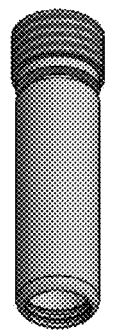
FIG 5A  FIG 5B  FIG 5C  FIG 5D

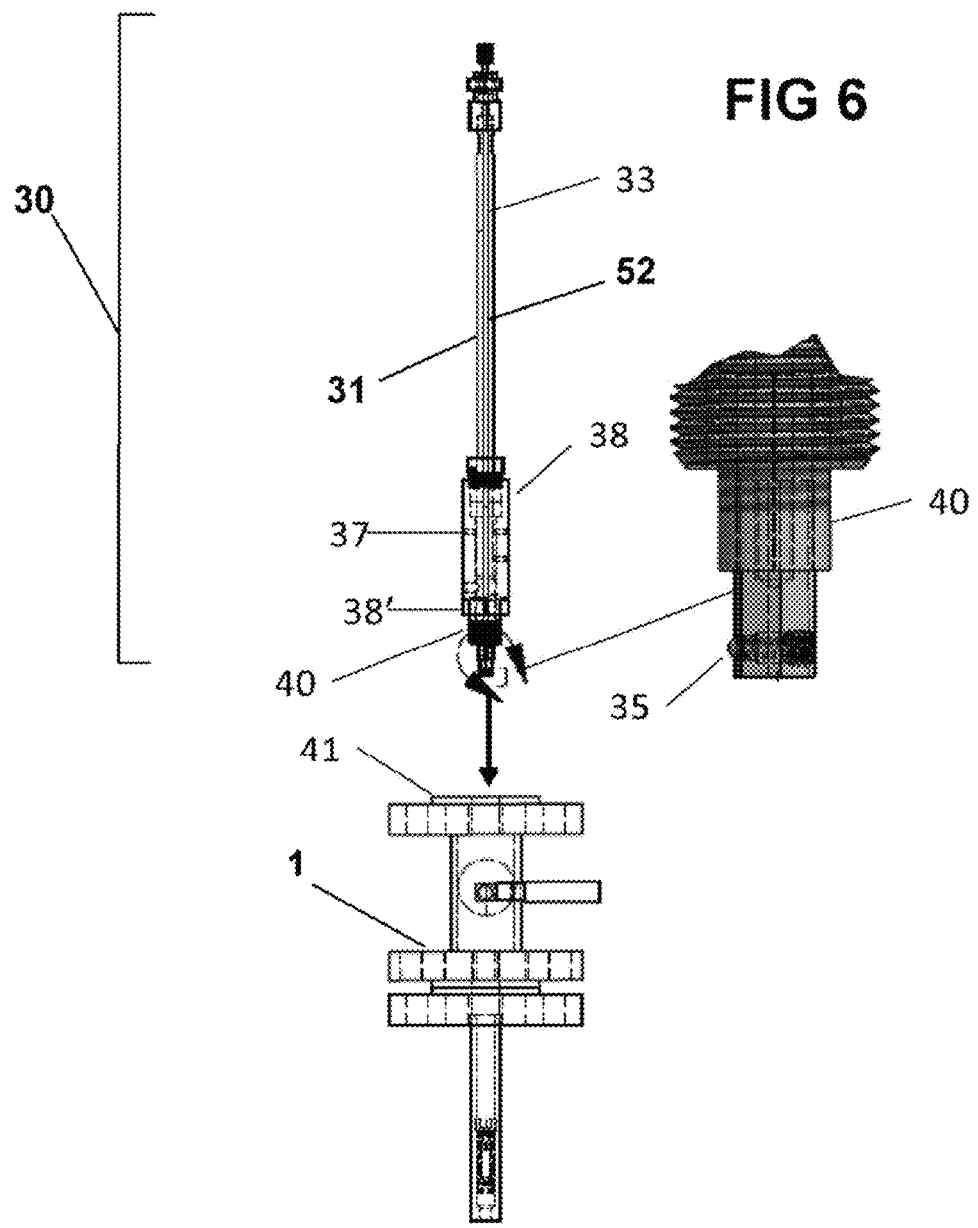

APPARATUS FOR ANALYTICAL SAMPLING AND/OR CONDITIONING OF A PROCESS GAS WITH SELECTIVE ISOLATION CAPABILITY, AND METHOD THEREFORE

BENEFIT CLAIM

The present application claims the benefit of U.S. Provisional Patent Application Ser. No. 61/716,656 filed Oct. 22, 2012, entitled "Apparatus for Analytical Sampling and/or Conditioning of a Process Gas with Selective Isolation Capability, and method Therefore", listing Valmond Joseph St Amant, III and Steven Douglas Calverley as inventors.

BACKGROUND OF THE INVENTION

It is common practice to use sampling probes and the like to extract fluid samples from pressurized pipelines or the like for analysis in the field or for off-site, laboratory analysis. This especially true in the natural gas industry, where the monetary value of the gas is dependent on its compositional analysis. Likewise, the chemical and oil refining industries also have needs for extracting fluid samples from pressurized fluid sources.

Recent offshore pipeline safety concerns since the 2010 Deepwater Horizon offshore incident have renewed an emphasis on the need for isolation devices such as double block and bleed sample valves, as well as compliance with OSHA standards in such activities. The use of an emergency valve shutoff in an isolation device is not believed compatible with the use of conventional sample probes situated as passing through the isolation device (i.e., with the valve in an open position), as said sample probes would be required to be manually or automatically removed to allow for valve closure. Accordingly, since the removal cannot be assured to occur in a timely fashion in an emergency, such an arrangement could not be relied as it may prevent the valve closure in an emergency event, resulting in failure of the emergency shutoff.

Current isolation device technology such as double block and bleed valves use a hollow tube "quill" below the valve as an option for sampling or injection through the open valve, but this system has not shown, suggested, or contemplated the mounting of analytical sample conditioning components or the like therein, and retaining same with the valve in a closed position. Thus, in the prior art, the quill is simply a hollow tube formed to act as a pass-through to facilitate the removal or injection of a sample, and no receiver or retainer function is contemplated.

GENERAL SUMMARY OF THE INVENTION

In an improvement over the prior art, as embodied in the present invention, a quill is formed to receive a component(s) such as a conditioning component or the like, in the vicinity of (upstream) the isolation device, so that the isolation device (valve) may be closed in an emergency with no interference from said conditioning component(s).

In effect, the present invention provides a redesign of the quill for the novel use as a means to receive and retain the component, a probe which is on the pressurized process gas side of the isolation device, and a probe which may be isolated on demand and without delay, should the need arise.

The component(s) utilized in the present device may comprise, for example, sample conditioning components such as membrane separators (e.g., phase separation membrane) regulators and regulator components, isokinetic sampling components, coalescing filters, particulate filters (screens, sintered metal, sintered plastics, thermoplastics, borosilicate glass, etc.), inertial separators, valves (i.e., throttling, needle, metering, ball, switching, etc) and others, and could be provided in a single component housing, or stacked for serial flow therethrough (see for example, FIG. 4A-4E).

The term "conditioning component" is not intended to be limiting as similar components may likewise be used in the present invention, including sensors and monitoring components such as corrosion coupons, wireless monitoring devices such as thermometers, wireless monitoring devices, moisture sensors, gas sensors (e.g. H2S and others), etc.

BRIEF DESCRIPTION OF THE FIGURES

For a further understanding of the nature and object of the present invention, reference should be had to the following detailed description, taken in conjunction with the accompanying drawings, in which like parts are given like reference numbers or letters, and wherein:

FIG. 2A is a side, partially cut-away, close-up view of the quill 17 of FIG. 1 engaging flange 4.

FIG. 2B is a side view of the cartridge 16 of FIG. 1.

FIG. 2C is a side, partially cut-away, close up view of the sample conditioning component in the cartridge in the quill of FIG. 1.

FIG. 2D is a bottom, view of the quill end of FIG. 1 distal the mounting flange.

FIG. 4A is a side, perspective view of a second, alternative embodiment of the quill of the present invention designed to engage a cartridge containing one, or multiple stacked conditioning components therein.

FIG. 4B is a side view of the modular, stackable cartridge of FIG. 4A.

FIG. 4C is a downstream (upper) end view of the modular, stackable cartridge of FIG. 4A.

FIG. 4D is an upstream (lower) end view of the modular, stackable cartridge of FIG. 4A.

FIG. 4E is another side, perspective view of the modular, stackable cartridge of FIG. 4A.

FIG. 5A is a side, perspective view of the modular, stackable cartridge of FIG. 3B.

FIG. 5B is an upstream (top) end view of the cartridge of FIG. 5A.

FIG. 5C is a side view of the cartridge of FIG. 5A showing the inner chamber for receiving a modular sampling conditioning component in phantom.

FIG. 5D is another side, perspective view of the modular, stackable cartridge of FIG. 5A.

FIG. 6 is a side view illustrating the insertion/removal tool of the present invention positioned to pass through and isolation device/valve to access/engage a cartridge/modular conditioning component situated in a quill.

DETAILED DESCRIPTION OF THE INVENTION

Figure 1:
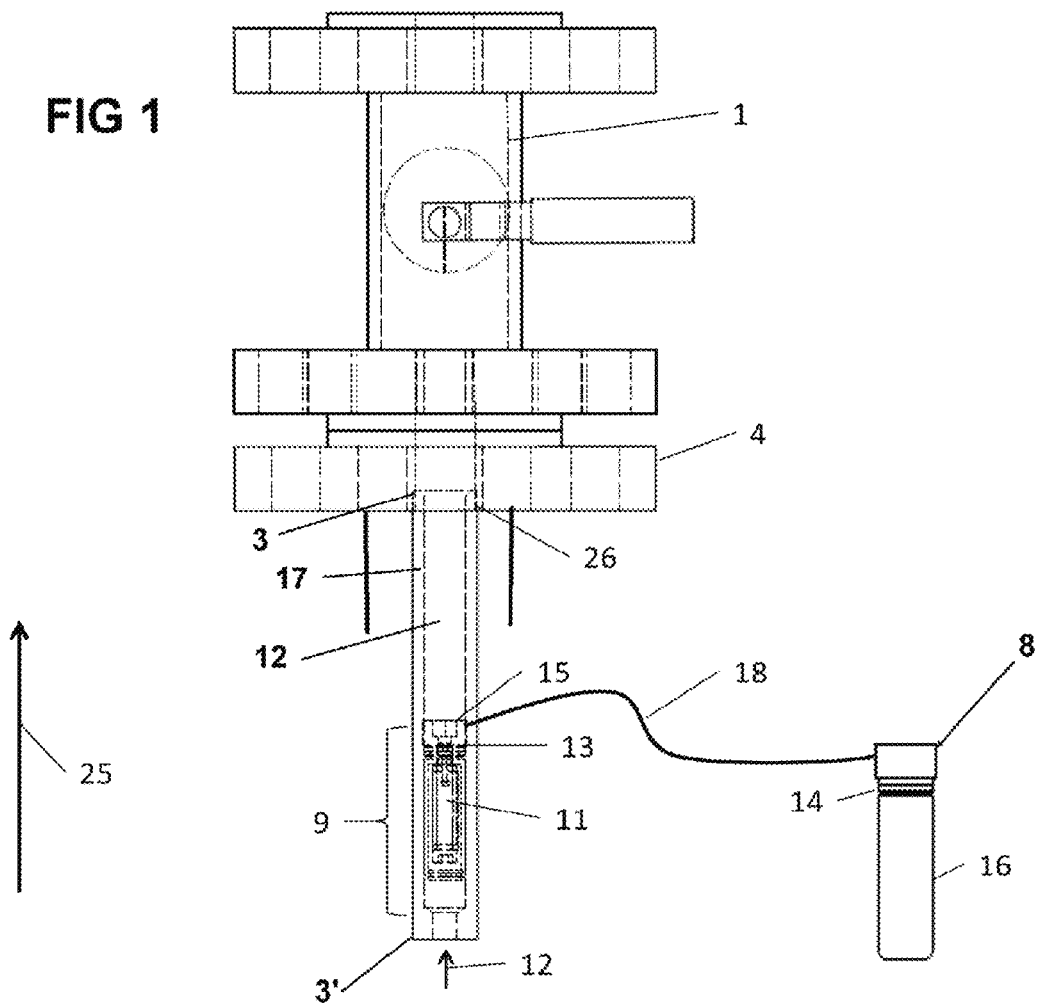
FIG. 1 is a side, partially cut-away view of the first, preferred embodiment of the present invention, illustrating a quill 17 engaged to an isolation device/valve 1, the quill 17 forming a receiver to receive cartridge 16 having sample conditioning component 11 situated therein to receive flow from longitudinal passage 12.
Figure 3A:
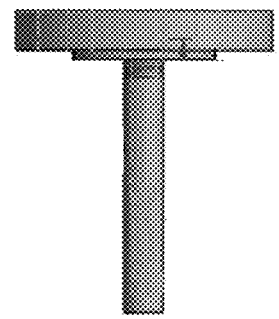
FIG. 3A is a side view of the quill with mounting flange of FIG. 2A.
Figure 3D:
FIG. 3D is a downstream (top) end view of the cartridge of FIG. 3B.
Figure 3C:
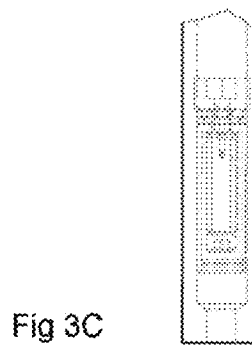
FIG. 3C is a side view of the quill of FIG. 3A showing the cartridge in phantom.
Figure 3B:
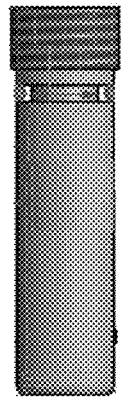
FIG. 3B is a side view of a cartridge of the present invention.

Referring to FIGS. 1, 2A-2D, 3A-3D, and 5A-5E, the first, preferred embodiment of the present invention contemplates a quill 17 having first 3 and second ends 3' with a passage 12 formed longitudinally therethrough forming a receiver 9 configured to receive a housing or cartridge 16 therein, the cartridge in the present embodiment having first 2 and second 2' ends, the first end 2 having an outer diameter 10' (OD) having a threaded area 8, formed to threadingly engage a thread 13 situated within the inner diameter (ID) receiver 9, associated with the OD 10 of quill 17, the cartridge sealingly engageable the ID of the receiver so as to facilitate a longitudinal fluid flow passage 12, 12' therethrough, the installed cartridge thus forming a "pass-through" for fluids flowing through the quill 17 allowing the conditioning and/or monitoring of same, or alternatively providing a capture device to capture fluids, as will be further discussed infra.

Socket 15 (shown in an exemplary hexagonal configuration shown in FIG. 5A-5B) may be formed in the threaded 8 end 2 of the cartridge 16, to facilitate placement 18 of the cartridge into the quill (FIG. 1), as will be further explained infra. An o-ring 14 or the like about the OD of the cartridge 16 may be used to form a fluid tight seal with the ID of quill when situated therein, such that fluid under pressure will be prevented from flowing between the OD of the installed cartridge and the ID of the surrounding quill, so as to facilitate the flowing of fluid into the quill into the cartridge. The fluid may then be sampled, monitored, or conditioned or otherwise treated and allowed to "pass-through", depending upon the desired application.

As mentioned, component 11 may comprise a single component which may be single function or multifunction, or alternatively may comprise one or more modular components 11' "stacked" (either within a common cartridge or one or more stacked cartridges in the receiver) in series in fluid sealed fashion so as to allow the contained flow of fluid therethrough so as to condition same, or have other features such as monitoring, sampling, or the like (FIG. 2A).

Figure 7:
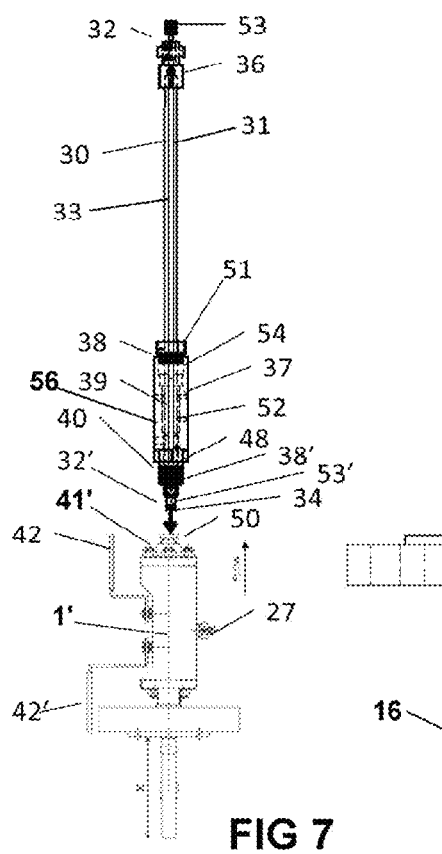
FIG. 7 is a side view of an insertion/removal tool of the present invention positioned to engage a double block and bleed (DBB) type valve to access the quill downstream for insertion/removal and/or maintenance of a cartridge/modular sample conditioning component therein.

Thus, the present installation allows a flow-through, when desired, of fluid flowing from the process gas stream 47 associated with the main. Accordingly, if component 11 comprises a conditioning component, with the valve 1 in an open position, fluid from the main flows 25 from the main 47, through any intermediary lateral, through the quill 17, into the cartridge 16, and through conditioning component(s) 11 situated therein, conditioning same so as to provide conditioned gas, for selective flow through valve 1 or vent 27 (FIG. 7).

This "flow through" feature may also be useful in a monitoring capacity, such as a corrosion coupon or the like. If no flow-through is desired, the downstream valve need only be closed, or alternatively, the cartridge 16 may not have a passage through the first 2 end, or the component may only have an opening at the end associated with the second end 2' of cartridge.

Alternatively, if the component is for sampling such as fluid collection, or monitoring such as pressure, temperature, liquids, etc, flow-through as a feature may or may not be utilized.

Further, if a monitoring component is utilized in lieu or in conjunction with a conditioning component, the fluid is being monitored upstream the valve, it thus may provide a monitoring of the gas on the process stream 47 side of the isolation device, even where said device is closed.

FIGS. 6-9, taken in conjunction with FIGS. 1-3 and 5, illustrate a new and innovative system utilizing a specially designed tool and method of use to facilitate access to cartridge (and thus any component 11 therein) via valve 1, and thus allow component 11 to be serviceable, installable, and/or removable without the need for removal/dismantling of the valve/isolation device or the like, or otherwise significantly interrupting the operation of the system.

As shown, the system of the present invention is formed so as to allow a tool to be inserted thru the open valve or other passage to allow access to the quill for insertion/removal of the cartridge 16, as well as offering the ability to inspect, maintain, replace, install the cartridge with component therein below/upstream the valve, even while the pipeline is still pressurized.

Figure 8A:
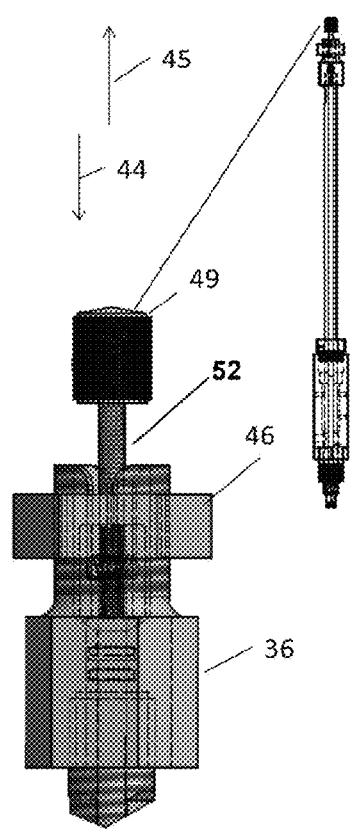
FIG. 8A is a side view of the insertion/removal tool of the present invention, showing a close-up of the upper portion of the tool including the button to manually engage the hex drive with spring-biased ball indent on the opposing end of the tool to the cartridge containing the modular sample conditioning component(s).
Figure 8B:
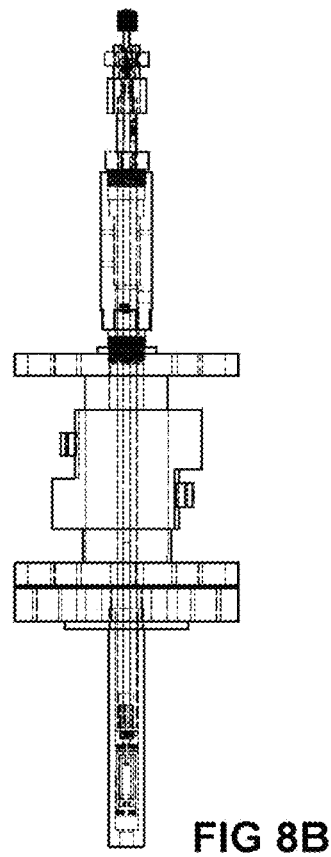
FIG. 8B is a side view of the insertion/removal tool of FIG. 8A passing through the double block & bleed valve (in open position) engaging a cartridge containing the conditioning component(s) situated in the quill.
Figure 8C:
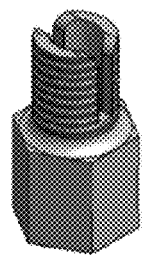
FIG. 8C is a side view of the slotted threaded end of the insertion removal tool associated with the operation of the top button.
Figure 9D:
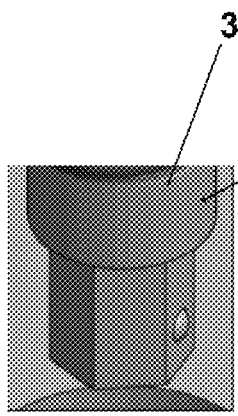
FIG. 9D is a side, isometric view of the hex drive body with spring biased indent of FIG. 7A.
Figure 9C:
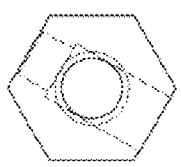
FIG. 9C is a top view of the body of FIG. 9A.
Figure 9A:
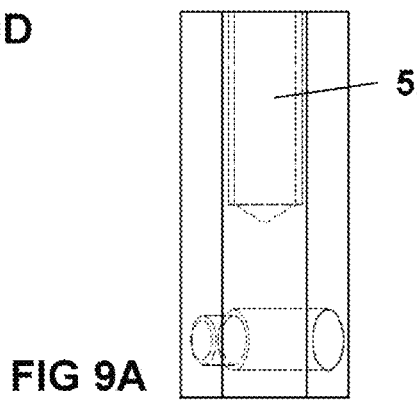
FIG. 9A is a side, close up, line drawing view of the hex drive body without the spring biased ball indent shown.
Figure 9B:
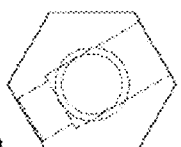
FIG. 9B is a bottom view of the body of FIG. 9A.
Figure 9:
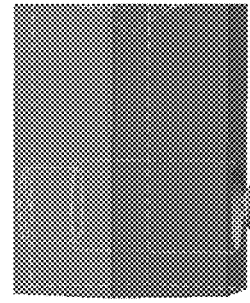
FIG. 9 is a side close-up, exploded view of the hex drive with spring-biased ball indent of FIG. 7A.
Figure 9E:
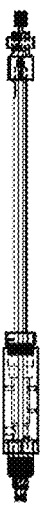
FIG. 9E is a side view of an insertion/removal tool of the present invention having the hex drive with spring-biased ball indent shown in FIGS. 9-9D.

Referring to FIGS. 6-8, the insertion/removal tool 30 of the present invention comprises a length of threaded rod 31 having first 32 and second 32' ends (FIG. 7), said rod having a longitudinal passage 33 formed therethrough, so as to provide a passage having an opening at each of said opposing ends 32, 32'.

Situated within said longitudinal passage 33 of said threaded rod 31 is a control rod 52 having first 53 and second 53' ends and a length which is longitudinally adjustable relative to rod 31, as will be more fully discussed herein.

Figure 7A:
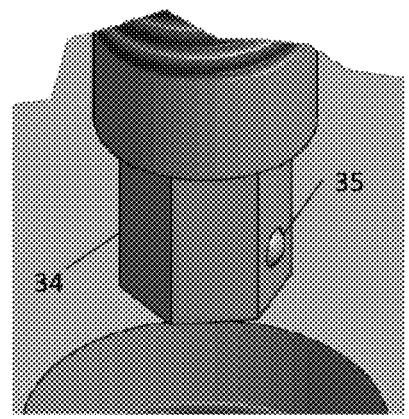
FIG. 7A is a close-up view of a hex drive with spring-biased ball indent formed to engage the cartridge containing the modular sample conditioning component(s).
Figure 7B:
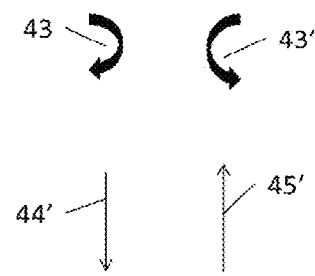
FIG. 7B is a side, partially cut-away view of a flange having a quill mounted thereto having a cartridge with modular sample conditioning component mounted thereto.

Said second end 32' of said threaded rod 31 has formed at its longitudinal passage 33 a cavity 55 formed to slidingly receive and support a drive 34 (for example, a square or hexagonal profile, see FIG. 7A), which engages said control rod 52 (in phantom) at its second end 53', so that said drive 34 can be selectively be manually retracted 45' or extended 44' by rotating hex nut 46 associated with the first 53 end of said control rod, which hex nut 46 engages a threaded area on said hex adapter 36, providing a mechanical advantage so as to allow the longitudinally repositioning of said control rod, thereby causing said drive 34 to retract 45' into, or extend 44' from said cavity, respectively. When the drive 34 slidingly engages the enveloping cavity at the second end 32' of rod, it is designed so that the cavity limits axial rotation of the drive to that of the threaded rod 31, so that when drive 34 slidingly engages the enveloping cavity at the second end 32' of rod, the axial rotation of the rod 31 rotates drive 34.

Continuing with the drawings, body 37 is provided having first 38 and second 38' ends, said body having a threaded longitudinal passage 39 formed therethrough to threadingly engage said threaded rod 31, said first 38 end of said body having a sealing nut 51 associated therewith for selectively providing sealing force on the packing gland 54, therewith making a seal on threaded rod 31, said second end of said body further comprising a profile 48 (for example, square profile with corner fillets) so that a wrench or the like may engage same, and a threaded end 40, formed to engage a threaded socket in an opening 41 associated with a threaded opening of a valve 1 (FIG. 1), or as shown beginning FIG. 7, an opening 41' of a isolation device/double block and bleed (DBB) valve. As shown, the body also includes a receiver 56 passage at the second 38' end to receive a cartridge 16, as will be further discussed herein.

Referring to the figures, for an exemplary use of the insertion/retrieval system of the present invention with a double block and bleed (DBB) valve 1', a quill 17 having a receiver 9 formed therein must be first mounted upstream the DBB. Generally, this installation will include an initial component, for example, a sample conditioning component 11 in a cartridge 16, threadingly seated in the receiver 9. Once the quill 17 installation is complete, the system can be serviced and maintained without the need for pressure shutdown, as will be shown, below.

Referring to FIGS. 7-8B, in a scenario where the component needs to be removed from the system using the insertion/retrieval tool, first valves 42, 42' are closed and the pressure within the valve is vented via the vent 27 passage therebetween. Cap 50, if any, is then removed from the opening to the valve.

Threaded end 40 of body then is positioned to engage threaded socket opening 41 (FIG. 6) of the opening of the valve 1 (or in DBB, opening 41', FIG. 7). The body of the tool is then threadingly engaged to the threaded socket opening 41 to form a sealed engagement by tightening body via profile 48.

After confirming the vent 27 on the DBB valve 1' is closed, 42, 42' can now be opened and the pressure contained as the threaded end 40 of body engaging threaded socket opening 41' of the DBB valve forms a plug. With the insertion/retrieval tool 30 in place and the valves opened, there is now provided a clear passageway to the quill 17 and any component therein.

To lower 44' the second end 32' of threaded rod to facilitate engagement to cartridge 16 already in the quill 17, the hex adapter 36 is turned 43, so as to lower the threaded rod 31 into the valve, through the valve passage and open valves 42, 42', until the second end 32' of the threaded rod with drive 34 is in the vicinity of the cartridge.

To cause drive 34 to emerge 44' from the second end 32' of threaded rod so as to engage socket 15 of cartridge 16, hex nut 46 is turned, urging 44 control rod 52 toward the DBB valve 1, causing drive 34 to extend 44' from the tool, through the open valve, until it extends into the locked position so as to engage socket 15 of cartridge 16, and biased ball 35 of drive 34 engages an indent formed in the sidewall of socket 15, to releasably engage same. Knob 49 may be provided so as to allow an operator to manually position drive 34 axially by turning control rod 52 (FIG. 8A) via knob 49, so as to align drive 34 with socket 15 so that drive 34 may be further lowered to engage socket 15 with the second end 32' of threaded rod engaging drive.

Once drive 34 has engaged socket, hex adapter 36 is rotated 43' in reverse direction, raising the rod while rotating drive 34 engaging socket 15, rotating cartridge 16, thereby disengaging threaded end 8 of cartridge from threaded portion 13 of quill receiver, urging cartridge 16 through quill then through the open valve(s) or isolation device, to the second end 32' of tool 30.

Once the cartridge 16 is drawn into to the second end 32' of body 37 of the tool 30, the cartridge and threaded rod should be clear the outer valve opening 41 (41' of the DBB valve/isolation device), said outer valve 42' is then closed and any residual gas between the closed outer valve 42 and the second end 38' of tool 30 is vented via the vent 27. At that point, the profile 48 on the body 37 can be turned 43' to disengage the threaded engagement between the threaded end 40 of body 37 and threaded socket at the opening 41' on the DBB valve/isolation device (or opening 41 in a regular valve as in FIG. 6), and the tool with cartridge removed.

While the above example illustrated removal of a cartridge in the quill, the same procedure may be used to insert and install the cartridge into the quill, utilizing a similar variation of the above procedure, but with some of the steps in reverse.

Referring to FIGS. 4A-4E and 1, in a second embodiment of the present invention, a component (for example, modular sample conditioning component or the like) is mounted to engage a quill situated on the process gas pressure side of the isolation device or valve. Such a system may comprise, for example, a fixed installation wherein the sampling component is fixedly attached to the component, thus without ready means for installation, maintenance, or removal other than shutting the system down and depressurizing the pipeline.

Alternatively, a quill 2 may be provided to removeably engage the component, for example, via threaded connection, but not necessarily accessible from outside the installation. For example, the component might threadingly engaging the end 3' of the quill distal the end 3 of the quill 2, which is threaded to threadingly engage a threaded OD in flange 4 (FIG. 1). See FIG. 4A-4E.

ELEMENTS of the INVENTION 1 isolation device/valve
2 quill
3, 3' first, second ends
4 mounting flange
8 threaded end
9 receiver
10, 10' inner, outer diameters
11 sample conditioning component,'
12 longitudinal passage
13 threaded portion
O'ring or other seal
15 socket for receiving tool
16 cartridge
17 quill
25 flow
26 threaded end
27 vent
30 insertion/retrieval tool
31 threaded rod
32, 32' first, second ends
33 longitudinal passage therethrough
34 Drive 35 spring biased ball indent
36 hex adapter
37 body
38 first, second ends
39 threaded longitudinal passage therethrough
40 threaded end
41 opening (threaded socket)
42,' levers for operating of isolation device/DBB valve
43 rotate in first direction, second direction
44 lower, emanate
45 raise, retract
46 nut to lower drive to engage socket 15
47 process gas stream
48 profile on body for engaging valve
49 button
50 plug
51 sealing nut
52 control rod
54 packing gland
55 cavity
56 receiver The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

We claim:

1. The method of monitoring or treating a fluid, comprising the steps of:
   a. providing a quill having first and second ends and a receiver to receive a component;
   b. installing said quill so that said first end is in fluid communication with an isolation device;
   c. mounting said component to said receiver of said quill to communicate with a fluid passage;
   d. allowing fluid to flow from said passage to engage said component;
   e. mounting a tool to said isolation device;
   f. opening said isolation device;
   g. deploying an extension from said tool through said isolation device and into said quill so as to engage said component;
   h. using said extension to disengage said component from said quill;
   i. retrieving said extension with component from said quill, through said open isolation device;
   j. closing said isolation device; and
   k. accessing said component.

2. The method of claim 1, wherein following step "d" there is provided the added step "d.(i)" of utilizing said component to monitor said fluid, providing data on same.

3. The method of claim 2, wherein following step "d.(i)" there is provided the added step "d.(ii)" of wirelessly transmitting said data on said fluid.

4. The method of claim 2, wherein following step "d.(i)" there is provided the added step "d.(ii)" of allowing said component to be exposed to said fluid for a period of time, then analyzing said component to discern properties relating to said fluid.

5. The method of claim 1, wherein following step "d." there is provided the added step "d.(i)" of utilizing said component to condition said fluid, providing conditioned fluid.

6. The method of claim 5, wherein following step "d.(i)" there is provided the added step "d.(ii)" of opening said isolation device, and allowing said conditioned fluid to flow therefrom.

7. The method of claim 1, wherein in step "c." there is provided the added step of mounting said component into a cartridge, then removeably mounting said cartridge with component to said receiver.

8. The method of monitoring or treating a fluid, comprising the steps of:
   a. providing a quill having a receiver to receive a cartridge;
   b. mounting said quill to a fluid passage;
   c. mounting said cartridge to said receiver of said quill;
   d. allowing fluid from said fluid passage to engage said cartridge;
   e. mounting a tool to an isolation device in fluid impermeable fashion, said isolation device formed to selectively provide access to said quill;
   f. opening said isolation device;
   g. deploying an extension from said tool through said isolation device and into said quill so as to engage said cartridge therein;
   h. using said extension to disengage said cartridge from said quill;
   i. retrieving said extension with cartridge from said quill, and through said open isolation device;
   j. closing said isolation device; and
   k. accessing said cartridge therein.

9. The method of claim 8, wherein in step "h." there is further provided the added steps of:
   h. (i). engaging a second end of said extension to a first end of said cartridge;
   h. (ii). applying force to a portion of said extension distal said second end of said extension so as to axially rotate said extension, disengaging said cartridge from said quill.

10. The method of claim 9, wherein in step "h.(ii)", said force is applied to an area associated with said first end of said extension.

11. The method of claim 9, wherein in step h. (i), there is further provided the step of:
   h.(i) a. utilizing a driver associated with the second end of said extension to engage with a socket formed to receive said driver in said cartridge.

12. The method of claim 11, wherein in step h.(ii), there is further provided the step of:
   h.(ii) a. utilizing a biased ball associated with said driver to engage said socket in said cartridge to removeably engage said cartridge so as to allow said extension to retrieve said cartridge from said quill.

13. The method of claim 11, wherein in step "h.(i) a." there is provided the additional steps of:
   h.(i) ai. utilizing a control rod engaged to said driver and passing longitudinally through said extension to align said driver with said socket; then
   h.(i) aii. engaging said driver to said socket.

14. The method of claim 8, wherein said cartridge comprises a component, and following step "d" there further comprises the additional step "d.(i)" of utilizing said component to condition or monitor fluid from said passage.

15. A fluid conditioning or monitoring system, comprising:
   a quill, comprising:
      a body having a length having first and second ends and a passageway therethrough;
      a receiver formed within said passageway;
      said first end of said quill in fluid communication with an isolation device;
   a cartridge formed to removeably engage said receiver of said quill, said cartridge having first and second ends, said second end being open;

a component having first and second ends, said component mounted to said cartridge;

wherein, upon engaging a tool to said isolation device and opening same, said tool passes through said isolation device to said cartridge, to engage and remove said cartridge with said component from said quill, via said isolation device while under pressure.

16. The fluid conditioning or monitoring system of claim 15, wherein said isolation device comprises a valve.

17. The fluid conditioning or monitoring system of claim 16, wherein said receiver in said quill has an inner wall, wherein said cartridge has an outer wall, and wherein a seal is provided between said receiver wall and said cartridge when said cartridge is in said receiver.

18. The fluid conditioning or monitoring system of claim 17, wherein said seal comprises an O-ring.

19. The fluid conditioning or monitoring system of claim 18, wherein, upon said cartridge sealingly engaging the receiver via said O-ring, any fluid entering said quill flows into said cartridge, engaging said component.

20. The fluid conditioning or monitoring system of claim 19, wherein said cartridge has a passage formed from its first to second end so as to facilitate longitudinal fluid flow therethrough, forming a "pass-through" for fluids flowing through the quill.

21. The fluid conditioning or monitoring system of claim 19, wherein said component comprises a modular fluid sampling component.

22. The fluid conditioning or monitoring system of claim 19, wherein said component comprises a modular fluid monitoring component.

23. The fluid conditioning or monitoring system of claim 22, wherein said component is wireless.

24. The fluid conditioning or monitoring system of claim 20, wherein said component comprises a modular fluid conditioning component.

25. The fluid conditioning or monitoring system of claim 24, wherein said modular fluid conditioning component includes a least one member of a group consisting of membrane separators, regulators and regulator components, isokinetic sampling components, coalescing filters, particulate filters, inertial separators, or valves.

26. The fluid conditioning or monitoring system of claim 25, wherein said modular fluid conditioning component is formed to condition any fluid passing therethrough, so as to provide conditioned fluid.

27. The fluid conditioning or monitoring system of claim 26, wherein said cartridge is formed to allow the passage of fluid therethrough, allowing conditioned fluid to pass through said quill to said isolation device.

28. The fluid conditioning or monitoring system of claim 27, wherein said isolation device comprises a valve.

29. The fluid conditioning or monitoring system of claim 28, wherein said isolation device comprises a double block and bleed valve.

30. The method of installing a component in a quill in a pressure zone, comprising the steps of:
    a. providing a receiver in said quill;
    b. providing an isolation device in communication with said quill;
    c. closing said isolation device;
    d. providing a tool having a body containing a component;
    e. mounting said body of said tool to said isolation device;
    f. opening said isolation device, while using said body to contain any pressure within said isolation device;
    g. using said tool to reposition said component out of said body, through said open isolation device, and into said quill;
    h. using said tool to removeably engage said component to said receiver in said quill;
    i. detaching said tool from said component and withdrawing same from said receiver and said isolation device; and
    j. allowing fluid to enter said component via said quill.

31. The method of claim 30, wherein said component comprises a sample conditioning component, and there is provided after step "j." the added sub-steps of:
    j. (i.) allowing said sample conditioning component to condition fluid entering the quill, providing conditioned fluid;
    j. (ii.) allowing said conditioned fluid to flow through said quill to said isolation device; and
    j. (iii.) collecting said conditioned fluid from said isolation device.

32. The method of claim 30, wherein said component comprises a monitoring component, and there is provided after step "j." the added sub-steps of:
    j. (i.) allowing said monitoring component to engage fluid entering the quill to monitor same for a period of time, providing data on the fluid; and
    j. (ii.) providing access to said data from said monitoring component.

33. An insertion tool, comprising:
    a body having first and second ends and a passage therebetween, said first end comprising a threaded opening having a cavity formed therein to receive a cartridge;
    an insertion rod having first and second ends, said insertion rod longitudinally engaging said passage formed in said body, said insertion rod having a longitudinal passage therethrough, said second end of said insertion rod having formed therein a receiver having walls forming a profile;
    a control rod having first and second ends, said control rod having a length situated in said longitudinal passage of said insertion rod, said second end of said control rod having a drive member having a profile formed to slidingly engage a socket at an end of said cartridge;
    whereby, upon engaging said threaded opening of said body to an isolation device and opening said isolation device, said second end of said insertion rod is formed to pass through said isolation device to insert or remove a cartridge upstream said isolation device under pressure.

34. The insertion tool of claim 33, wherein said drive member has a biased ball formed to releasably engage said socket of said cartridge upon said driver slidably engaging therewith.

35. The insertion tool of claim 34, wherein said insertion rod has at its second end a receiver for receiving said drive member of said control rod, said receiver having a profile formed to engage said driver member upon the axial rotation of same, and whereby, upon positioning said second end of said insertion rod in the vicinity of said first end of said cartridge, said driver member may be lowered from said receiver in said insertion rod by manipulating said control rod, and using said control rod, said driver member may be axially aligned with said socket in said cartridge, so as to allow the engagement thereto.

36. A fluid conditioning or monitoring system, comprising:
    a quill, comprising:
        a body having a length having first and second ends and a passageway therethrough;
        a receiver;

a cartridge formed to removeably engage said receiver of said quill, said cartridge having first and second ends, said first end having a connector formed to engage a tool, said second end formed to engage a pressurized fluid;

wherein, upon engaging a tool to said isolation device and opening said isolation device, an extension associated with said tool is formed to pass through said isolation device to said cartridge in said quill, to engage via said connector of said cartridge to remove same from said quill and isolation device while under pressure.

37. The fluid conditioning or monitoring system of claim 36, wherein said isolation device comprises a valve.

38. The fluid conditioning or monitoring system of claim 37, wherein said receiver in said quill has an inner wall, wherein said cartridge has an outer wall, and wherein a seal is provided between said receiver wall and said cartridge when said cartridge is in said receiver.

39. The fluid conditioning or monitoring system of claim 38, wherein said seal comprises an O-ring.

40. The fluid conditioning or monitoring system of claim 39, wherein, upon said cartridge sealingly engaging the receiver via said O-ring, any fluid entering said quill flows into said cartridge, engaging said component.

41. The fluid conditioning or monitoring system of claim 40, wherein said cartridge has a passage formed from its first to second end so as to facilitate longitudinal fluid flow therethrough, forming a "pass-through" for fluids flowing through the quill.

42. The fluid conditioning or monitoring system of claim 40, wherein said cartridge comprises a modular fluid sampling component.

43. The fluid conditioning or monitoring system of claim 40, wherein said cartridge comprises a modular fluid monitoring component.

44. The fluid conditioning or monitoring system of claim 43, wherein said component is wireless.

45. The fluid conditioning or monitoring system of claim 41, wherein said cartridge comprises a modular fluid conditioning component.

46. The fluid conditioning or monitoring system of claim 45, wherein said modular fluid conditioning component includes a least one member of a group consisting of membrane separators, regulators and regulator components, isokinetic sampling components, coalescing filters, particulate filters, inertial separators, or valves.

47. The fluid conditioning or monitoring system of claim 46, wherein said modular fluid conditioning component is formed to condition any fluid passing therethrough, so as to provide conditioned fluid.

48. The fluid conditioning or monitoring system of claim 47, wherein said cartridge is formed to allow the passage of fluid therethrough, allowing conditioned fluid to pass through said quill to said isolation device.

49. The fluid conditioning or monitoring system of claim 48, wherein said isolation device comprises a valve.

50. The fluid conditioning or monitoring system of claim 49, wherein said isolation device comprises a double block and bleed valve.

* * * * *